(12) United States Patent
Morimoto

(10) Patent No.: US 10,799,086 B2
(45) Date of Patent: Oct. 13, 2020

(54) LIGHT SOURCE DEVICE FOR ENDOSCOPE AND ENDOSCOPE SYSTEM

(71) Applicant: FUJIFILM Corporation, Tokyo (JP)

(72) Inventor: Yoshinori Morimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/430,446

(22) Filed: Jun. 4, 2019

(65) Prior Publication Data

US 2020/0029786 A1 Jan. 30, 2020

(30) Foreign Application Priority Data

Jul. 26, 2018 (JP) .................................. 2018-140355

(51) Int. Cl.

| A61B 1/07 | (2006.01) |
| A61B 1/00 | (2006.01) |
| A61B 1/06 | (2006.01) |
| F21V 23/04 | (2006.01) |
| F21V 8/00 | (2006.01) |
| F21V 23/00 | (2015.01) |

(52) U.S. Cl.
CPC ...... *A61B 1/00006* (2013.01); *A61B 1/00096* (2013.01); *A61B 1/0638* (2013.01); *A61B 1/07* (2013.01); *F21V 23/003* (2013.01); *F21V 23/0457* (2013.01); *G02B 6/0008* (2013.01)

(58) Field of Classification Search
CPC .......................... A61B 1/00096; A61B 1/0638

USPC .......................................................... 362/553
See application file for complete search history.

(56) References Cited

U.S. PATENT DOCUMENTS

| 2001/0055462 A1* | 12/2001 | Seibel ................ A61B 1/00048 |
| | | 385/147 |
| 2015/0099932 A1* | 4/2015 | Morimoto ............ A61B 1/0638 |
| | | 600/180 |
| 2016/0134792 A1* | 5/2016 | Kubo ..................... A61B 1/045 |
| | | 348/68 |
| 2017/0360287 A1* | 12/2017 | Morimoto ............ A61B 1/0638 |
| 2019/0068864 A1* | 2/2019 | Ohashi ................. A61B 1/0684 |

FOREIGN PATENT DOCUMENTS

| WO | 2015016013 | 2/2015 |

* cited by examiner

*Primary Examiner* — Christopher M Raabe
(74) *Attorney, Agent, or Firm* — JCIPRNET

(57) ABSTRACT

The light source device for an endoscope includes a plurality of light sources that emits light with different wavelengths, a light path integration part that integrates light paths of the light, a light path unit on which the integrated light is incident, a photodetector that receives a portion of the light until the light paths are integrated by the light path integration part to obtain information on a light quantity, and a light source controller that adjusts the light quantity of the light based on a light quantity measurement signal generated by the photodetector. The light path unit includes a light guide part that has a homogenizing function to receive the integrated light from the light path integration part, and a light collecting part that collects light passing through the light guide part.

19 Claims, 8 Drawing Sheets

LIGHT SOURCE DEVICE FOR ENDOSCOPE AND ENDOSCOPE SYSTEM

CROSS-REFERENCE TO RELATED APPLICATIONS

The present application claims priority under 35 U.S.C. § 119 to Japanese Patent Application No. 2018-140355, filed on Jul. 26, 2018. The above application is hereby expressly incorporated by reference, in its entirety, into the present application.

BACKGROUND OF THE INVENTION

1. Field of the Invention

The present invention relates to a light source device for an endoscope which emits a plurality of kinds of light with different wavelengths to supply illumination light to an endoscope and an endoscope system that acquires an endoscopic image of an observation object using the light source device for an endoscope, and more particularly, to a light source device for an endoscope which suppresses return light to the light source device for an endoscope and an endoscope system comprising the light source device for an endoscope.

2. Description of the Related Art

In the recent medical care, diagnosis using an endoscope system comprising a light source device for an endoscope, an electronic endoscope (endoscope), a processor device, and the like, has been widely performed. The light source device for an endoscope generates illumination light to irradiate an observation object. The electronic endoscope captures the observation object irradiated with the illumination light with an image sensor to generate image signals. The processor device performs image processing of the image signals generated by the electronic endoscope to generate an observation image for display on a monitor.

In the related art, in the light source device for an endoscope, lamp light sources, such as a xenon lamp and a halogen lamp, which emit white light as the illumination light, are used. However, in recent years, instead of the lamp light sources, semiconductor light sources such as a laser diode (LD) that emit light of a specific color or a light emitting diode (LED), are used.

For example, a light source device for an endoscope which supplies illumination light to light guide of an endoscope is disclosed in WO2015/016013A. In WO2015/016013A, there are provided a semiconductor light source emitting light in each wavelength range such as blue, green, or red, where the semiconductor light source includes a light quantity measurement sensor measuring a light quantity of color light emitted by each semiconductor light source, and a glass plate provided immediately before the semiconductor light source and reflecting a part of color light emitted from the semiconductor light source to guide the part to the light quantity measurement sensor.

Each light quantity measurement sensor outputs a light quantity measurement signal corresponding to the light quantity of the received color light, and outputs the signal to a light source controller. The light source controller compares the light quantity measurement signal with a target light quantity, and based on the comparison result, finely adjusts a drive current value set for exposure control and supplied to each semiconductor light source such that the light quantity becomes the target value. As described above, the light quantity of the color light is constantly monitored by the light quantity measurement sensor, and the light quantity is controlled to be always kept at the target value by finely adjusting the drive current value to be supplied based on the measurement result of the light quantity.

SUMMARY OF THE INVENTION

As described above, in WO2015/016013A, a plurality of semiconductor light sources is provided, and based on the light quantities of the respective semiconductor light sources measured by the light quantity measurement sensor, the light quantity is controlled to be kept at the target value by the light source controller. In WO2015/016013A, in a case where there is much return light, the light quantity measured by the light quantity measurement sensor is larger than the actual light quantity by a return light quantity, and there is a problem that appropriate light quantity control cannot be performed.

An object of the invention is to provide a light source device for an endoscope which solves the problem based on the above-mentioned related art and suppresses return light, and an endoscope system comprising the light source device for an endoscope.

In order to achieve the above-mentioned object, according to one aspect of the invention, there is provided a light source device for an endoscope. The light source device comprises a plurality of light sources that emits light with different wavelengths, a light path integration part that integrates light paths of light emitted from the plurality of light sources to emit integrated light, a light path unit on which the integrated light emitted from the light path integration part is incident, a photodetector that receives a portion of light emitted from at least one of the plurality of light sources until the light paths are integrated by the light path integration part to obtain information on a light quantity, and a light source controller that adjusts the light quantity of the light emitted from the at least one light source based on a light quantity measurement signal generated by the photodetector, in which the light path unit includes a light guide part that has a homogenizing function to receive the integrated light from the light path integration part and a light collecting part that collects light passing through the light guide part.

It is preferable that the light guide part is a light pipe.

It is preferable that the light guide part has a core material and a clad material provided around the core material and having a smaller refractive index than the core material.

It is preferable that the light collecting part is formed by arranging two biconvex lenses such that curved surfaces thereof face each other, arranging two plano-convex lenses such that flat surfaces thereof face each other, or arranging two plano-convex lenses such that curved surfaces thereof face each other.

It is preferable that the photodetector is provided to each of the plurality of light sources, and the light source controller adjusts the light quantity of the light emitted from each of the plurality of light sources based on the light quantity measurement signal generated by each of the photodetectors.

It is preferable that the plurality of light sources is three or four in number.

It is preferable that the plurality of light sources includes a light source that emits red light, a light source that emits green light, and a light source that emits blue light.

It is preferable that the plurality of light sources includes a laser diode or a light emitting diode.

It is preferable that the photodetector is a photodiode.

According to another aspect of the invention, there is provided an endoscope system comprising an endoscope that includes a light guide and a light source device for an endoscope that supplies light to the light guide, in which the light source device for an endoscope includes a plurality of light sources that emits light with different wavelengths, a light path integration part that integrates light paths of light emitted from the plurality of light sources to emit integrated light, a light path unit on which the integrated light emitted from the light path integration part is incident, a photodetector that receives a portion of light emitted from at least one of the plurality of light sources until the light paths are integrated by the light path integration part to obtain information on a light quantity, and a light source controller that adjusts the light quantity of the light emitted from the at least one light source based on a light quantity measurement signal generated by the photodetector, the light path unit includes a light guide part that has a homogenizing function to receive the integrated light from the light path integration part and a light collecting part that collects light passing through the light guide part, and the integrated light is supplied to the light guide through the light collecting part of the light path unit.

It is preferable that the photodetector is provided to each of the plurality of light sources, and the light source controller adjusts the light quantity of the light emitted from each of the plurality of light sources based on the light quantity measurement signal generated by each of the photodetectors.

With the invention, it is possible to suppress return light and improve accuracy of the light quantity of each light source.

DESCRIPTION OF THE PREFERRED EMBODIMENTS

Hereinafter, an endoscope system related to the invention will be described in detail on the basis of a preferred embodiment illustrated in the attached drawings.

In addition, the drawings to be described below are illustrative drawings for describing the invention, and the invention is not limited to the following drawings.

In addition, in the following, "to" showing a numerical range includes numerical values described on both sides thereof. For example, $\varepsilon$ being a numerical value $\alpha$ to a numerical value $\beta$ means that the range of $\varepsilon$ is a range including the numerical value $\alpha$ and the numerical value $\beta$, and in a case where these are expressed by mathematical symbols, $\alpha \leq \varepsilon \leq \beta$ is satisfied.

Angles, such as "parallel," include error ranges that are generally allowed in a corresponding technical field unless otherwise specified. The "same" includes error ranges that are generally allowed in a corresponding technical field unless otherwise specified.

In general, the wavelength of blue is about 445 nm to about 485 nm, for example, a color intermediate between blue and green may be distinguished from blue, for example, by referring to bluish green. However, in an endoscope system 10, there is no need for excessively subdividing the type of color (the name of color) regarding at least light components emitted by individual light sources of the light source unit. For this reason, a color of light having a wavelength of about 440 nm or more and less than about 490 nm is referred to as blue. Additionally, a color of light having a wavelength of about 490 nm or more and less than about 600 nm is referred to as green, and a color of light having a wavelength of about 600 nm or more and less than about 680 nm is referred to as red. Also, a color of visible light having a wavelength of less than "about 440 nm" which is a lower limit of the wavelength of the above-described blue, for example, visible light of about 380 nm or more and less than about 440 nm is referred to as violet, and a color of light which has a wavelength shorter than violet but for which an image sensor 48 has sensitivity is referred to as ultraviolet. Additionally, a color of light which has a wavelength of "about 680 nm" or more that is an upper limit of the wavelength of the above-described red and for which the image sensor 48 has sensitivity is referred to as infrared. Additionally, the term "broadband" means that the wavelength range reaches the wavelength range of a plurality of colors. White means a color of light including at least the light that belongs to the above-described blue or violet, the light that belongs to green, and the light that belongs to red.

First Embodiment

Figure 1:
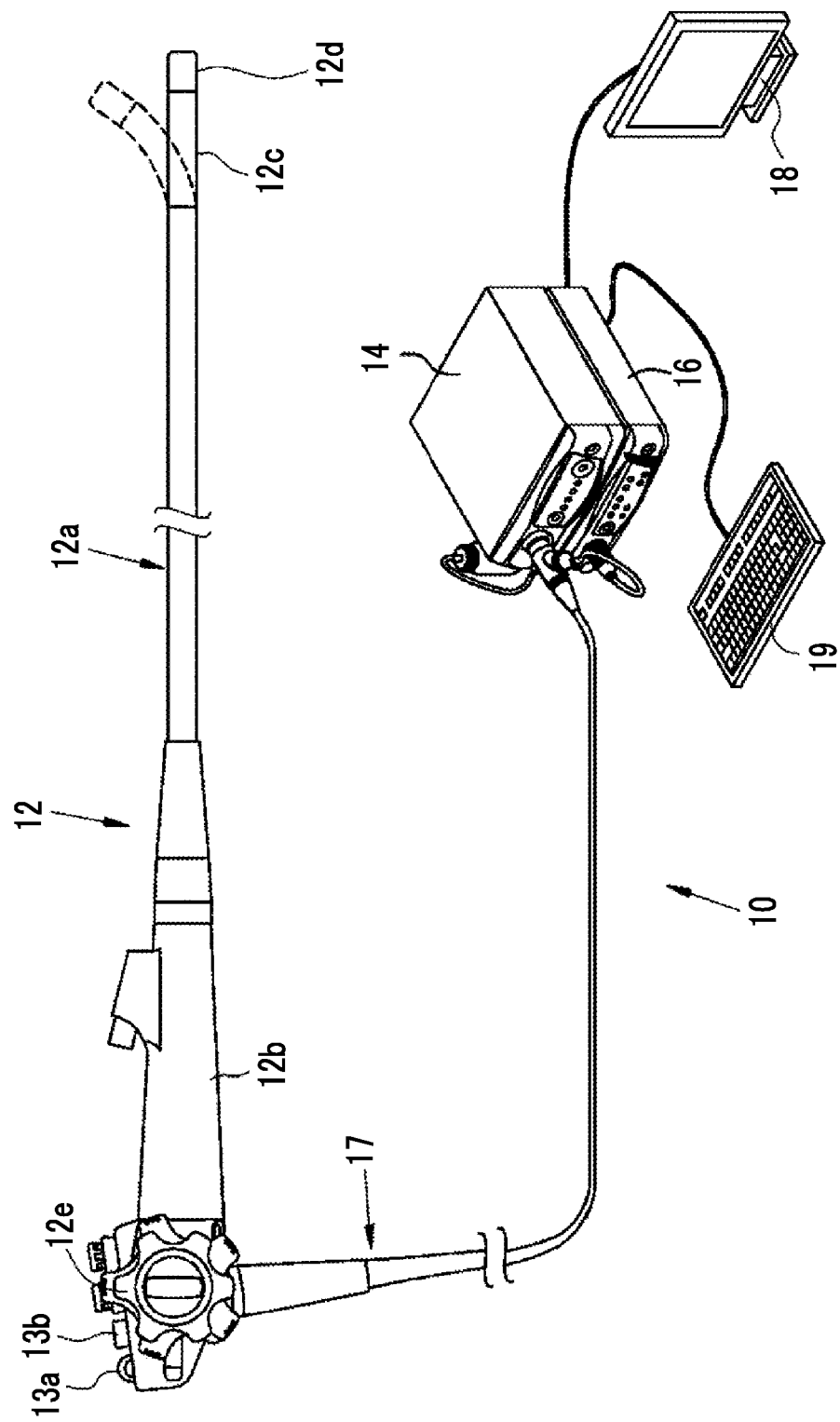
FIG. 1 is a perspective view conceptually illustrating an example of an endoscope system of a first embodiment of the invention.
Figure 2:
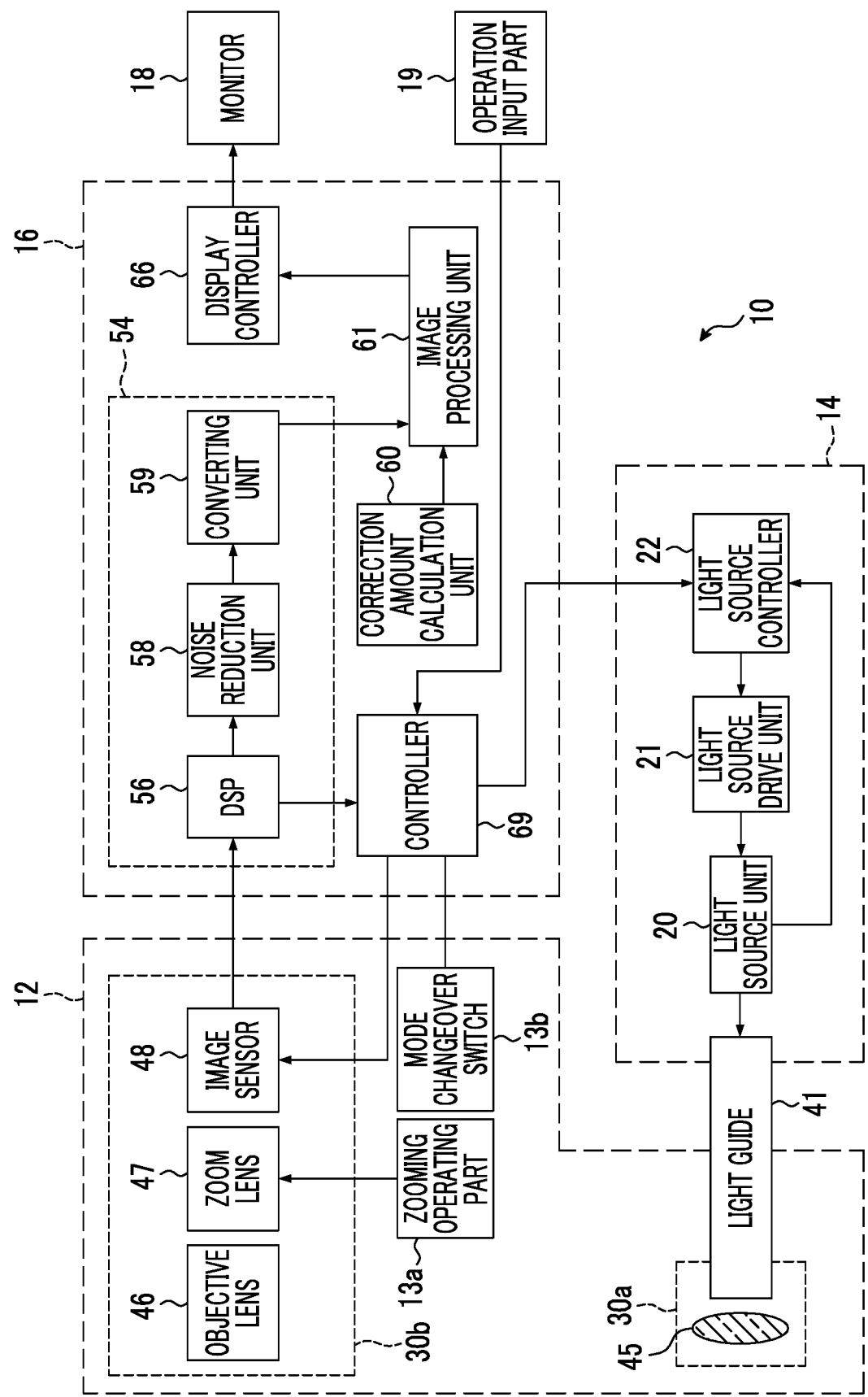
FIG. 2 is a block diagram conceptually illustrating the example of the endoscope system of the first embodiment of the invention.

FIG. 1 is a perspective view conceptually illustrating an example of an endoscope system of a first embodiment of the invention, and FIG. 2 is a block diagram conceptually illustrating an example of the endoscope system of the first embodiment of the invention.

As illustrated in FIG. 1, the endoscope system 10 comprises an endoscope (hereinafter, simply referred to as an endoscope) 12 that images an observation region within a living body (within a subject) that is an observation object, a processor device 16 that generates a display image of the observation region on the basis of image signals obtained by the imaging, a light source device 14 for endoscopes (hereinafter simply referred to as a light source device) that supplies illumination light, with which the observation region is irradiated, to the endoscope 12, and a monitor 18 that displays the display image. An operation input part 19, such as a keyboard and a mouse, is connected to the processor device 16.

The endoscope system 10 is capable of executing a normal observation mode for observing the observation region, and a blood vessel enhancement observation mode for enhancing and observing blood vessels that are present inside a mucous membrane of the observation region. The blood vessel enhancement observation mode is a mode for visualizing a pattern of the blood vessels as blood vessel information and performing diagnosis, such as differentiation of a malignant or benign tumor. In this blood vessel enhancement observation mode, the observation region is irradiated with illumination light including many components of light having a specific wavelength range in which the absorbance for hemoglobin in blood is high.

In the normal observation mode, a normal observation image suitable for observation of the entire observation region is generated as the display image. In the blood vessel enhancement observation mode, a blood vessel enhancement observation image suitable for observation of the pattern of the blood vessels is generated as the display image.

The endoscope 12 has an insertion part 12a to be inserted into the subject, an operating part 12b provided at a proximal end portion of the insertion part 12a, a bending part 12c provided on a distal end side of the insertion part 12a, and a distal end part 12d. By operating an angle knob 12e of the operating part 12b, the bending part 12c is bent. The distal end part 12d is directed in a desired direction as a result of the bending of the bending part 12c. In addition, the distal end part 12d is provided with a jet port (not illustrated) that jets air, water, or the like toward the observation object. Additionally, the operating part 12b is provided with a forceps port for inserting a treatment tool, an air/water supply button that is operated in a case where performing air supply or water supply from an air/water supply nozzle, a freeze button (not illustrated) for capturing a still image, a zooming operating part 13a, and a mode changeover switch 13b in addition to the angle knob 12e. The zooming operating part 13a is used for enlarging or reducing the observation object. The mode changeover switch 13b is used for switching a plurality of observation modes in a case where the endoscope system 10 has the plurality of observation modes.

Additionally, the endoscope 12 comprises a universal cord 17 for connecting the endoscope 12 to the processor device 16 and the light source device 14.

A communication cable and light guide 41 (refer to FIG. 2) extending from the insertion part 12a is inserted through the universal cord 17, and a connector is attached to one end on the side of the processor device 16 and the light source device 14. The connector is a composite connector including a communication connector and a light source connector. The communication connector and the light source connector are attachably and detachably connected to the processor device 16 and the light source device 14, respectively. One end of the communication cable is disposed at the communication connector. An incident end 41a of the light guide 41 is disposed at the light source connector.

As illustrated in FIG. 2, the light source device 14 comprises a light source unit 20 having two or more light sources with different dominant wavelengths, a light source controller 22 that controls the light emission timing of the light source unit 20, light emission quantity, and the like, and a light source drive unit 21 that generates a driving current, for example, as a drive signal, in accordance with a control signal of the light source controller 22 and supplies the driving current (drive signal) to each light source to make the light source emit light.

In the light source device 14, the light source controller 22 controls the light source drive unit 21 such that illumination light Ls (refer to FIG. 5) is radiated from the light source unit 20 to an object Ob (refer to FIG. 5) that is the observation object with a specific light quantity. For example, even in a case where a distance Ld (refer to FIG. 5) of a distal end part 12d (refer to FIG. 5) of the endoscope and the object Ob (refer to FIG. 5) changes, the quantity of the illumination light Ls is controlled such that the brightness of an endoscopic image becomes constant. In this case, the quantity of the illumination light Ls is controlled such that the brightness value becomes constant, for example, using a brightness value obtained from a sensor signal of the image sensor 48.

In this case, the light source unit 20 is provided with photodetectors 91, 92, and 93 (refer to FIG. 5), as will be described below, and information on the quantities of light of the individual light sources detected by the photodetectors 91, 92, and 93 (refer to FIG. 5) is input to the light source controller 22, and the information on the light quantities of the individual light sources is obtained. The light source controller 22 accurately and automatically controls the light emission quantities of the light sources of the light source unit 20 on the basis of the information on the light quantities of the individual light sources and the brightness value of the image sensor 48. Thus, using the information on the light quantities of individual light sources of the light source unit 20, the light emission quantity of each light source is controlled. For this reason, the information on the light quantities of individual light sources is important information, and accurate information is required about the light quantity of each light source.

The illumination light emitted from the light source unit 20 is incident on the light guide 41. The light guide 41 is built within the endoscope 12 and the universal cord 17 and propagates the illumination light up to the distal end part 12d of the endoscope 12. The universal cord 17 is a cord that connects the endoscope 12, and the light source device 14 and the processor device 16 together. In addition, multimode fiber can be used as the light guide 41. As an example, a fine-diameter fiber cable of which the core diameter is 105 μm, the clad diameter is 125 μm, and a diameter including a protective layer used as an outer cover is 0.3 to 0.5 mm can be used.

The distal end part 12d of the endoscope 12 is provided with an illumination optical system 30a and an imaging optical system 30b. The illumination optical system 30a has an illumination lens 45, and the illumination light is radiated to the observation object via the illumination lens 45. The imaging optical system 30b has an objective lens 46, a zoom lens 47, and an image sensor 48. The image sensor 48 images the observation object using reflected light or the like of the illumination light returning from the observation object via the objective lens 46 and the zoom lens 47. Scattered light, fluorescence emitted from the observation object, fluorescence resulting from a medicine administered to the observation object, in addition to the reflected light, or the like is included in the above-described reflected light or the like of the illumination light returning from the above-described observation object.

In addition, the zoom lens 47 is moved by operating the zooming operating part 13a. As a result, the observation object imaged using the image sensor 48 is enlarged or reduced and observed.

As the image sensor 48, for example, photoelectric conversion elements, such as a charge coupled device (CCD) sensor and a complementary metal-oxide semiconductor (CMOS) sensor, are used. In the image sensor 48 using a photoelectric conversion element, received light is photoelectrically converted, and a signal charge according to the quantity of the received light is accumulated as a sensor signal for each pixel. The signal charge for each pixel is converted into a voltage signal and is read from the image sensor 48. The voltage signal for each pixel read from the image sensor 48 is input to a digital signal processor (DSP) 56 as an image signal.

The image sensor 48 performs, for example, an accumulation operation in which a signal charge is accumulated in a pixel, and a reading operation in which the accumulated signal charge is read, within an acquisition period of one frame. The light source device 14 generates the illumination light in conformity with the timing of the accumulation operation of the image sensor 48, and supplies the illumination light to the light guide 41 through the light path unit 42.

Figure 3:
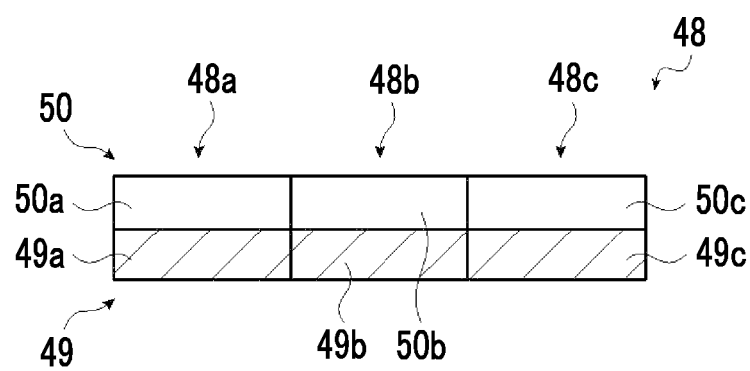
FIG. 3 is a schematic view illustrating an example of an image sensor of the endoscope system of the first embodiment of the invention.

As illustrated in FIG. 3, the image sensor 48 has a pixel unit 49 having a photoelectric conversion function, and a filter unit 50 having spectral transparency for a specific wavelength range, and a first element part 48a, a second element part 48b, and a third element part 48c are constituted by the pixel unit 49 and the filter unit 50. A signal charge is accumulated as a sensor signal as described above in the pixel unit 49 having the photoelectric conversion function.

In the image sensor 48, the first element part 48a has a first pixel 49a having the photoelectric conversion function, and a first filter 50a having the spectral sensitivity for a first color component. A first signal value of the first color component is obtained in the first element part 48a in accordance with the light incident on the image sensor 48.

The second element part 48b has a second pixel 49b having the photoelectric conversion function, and a second filter 50b having the spectral sensitivity for a second color component. A second signal value of the second color component is obtained in the second element part 48b in accordance with the light incident on the image sensor 48.

The third element part 48c has a third pixel 49c having the photoelectric conversion function, and a third filter 50c having the spectral sensitivity for a third color component. The third color component is a color other than the first color component and the second color component. A third signal value of the third color component is obtained in the third element part 48c in accordance with the light incident on the image sensor 48.

The image sensor 48 has, for example, a color sensor of a primary color system having a color filter in each pixel. The first filter 50a, the second filter 50b, and the third filter 50c are constituted of, for example, color filters. In this case, the first filter 50a, the second filter 50b, and the third filter 50c of the image sensor 48 are, for example, any of a red color filter (R color filter), a green color filter (G color filter), and a blue color filter (B color filter). The first element part 48a, the second element part 48b and the third element part 48c are appropriately determined in accordance with the above-described first color component, second color component, and third color component.

Among the individual pixels of the first pixel 49a, the second pixel 49b, and the third pixel 49c, a pixel having the R color filter is an R pixel, a pixel having the G color filter is a G pixel, and a pixel having the B color filter is a B pixel. As sensor signals of the image sensor 48, an R signal is obtained from the R pixel, a G signal is obtained from the G pixel, and a B signal is obtained from the B pixel. The R signal, the G signal, and the B signal are input to the DSP 56 as image signals.

In this way, since the image sensor 48 has, for example, three-color pixels of the R pixel, the G pixel, and the B pixel, an R image obtained by imaging the observation object with the R pixel, a G image obtained by imaging the observation object with the G pixel, and a B image obtained by imaging the observation object with the B pixel are simultaneously obtained in a case where the observation object is imaged using white light for the illumination light.

Figure 4:
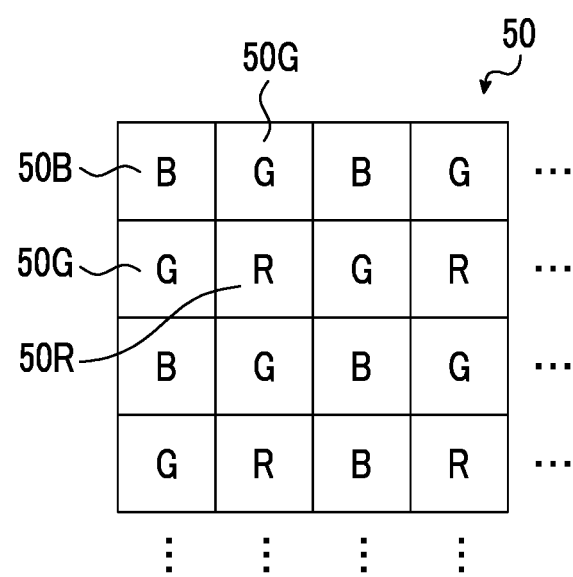
FIG. 4 is a schematic view illustrating an example of arrangement of color filters of the image sensor of the endoscope system of the first embodiment of the invention.

Although the arrangement of an R color filter 50R (refer to FIG. 4), a G color filter 50G (refer to FIG. 4), and a B color filter 50B (refer to FIG. 4) is not particularly limited, these color filters are arranged in a ratio of R:G:B=1:2:1 in consideration of visibility, for example, as illustrated in FIG. 4.

In addition, for example, a signal value of the above-described R signal is equivalent to a second signal value, a signal value of the G signal is equivalent to a first signal value, and a signal value of the B signal is equivalent to a third signal value.

In addition, although the color sensor of the primary color system has been exemplified as the image sensor 48, the image sensor is not limited thereto, and a color sensor of a complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. The images obtained from the above-described individual color pixels in a case where the color sensor of the complementary color system is used can be converted into the B image, the G image, and the R image in a case where color conversion of complementary color and primary color is performed. Additionally, instead of the color sensor, a monochrome sensor that is not provided with the color filters can be used as the image sensor 48. In this case, the above-described individual images can be obtained by sequentially imaging the observation object using illumination light components in individual colors, such as BGR.

Additionally, a communication cable that performs communication of a drive signal for driving the image sensor 48 and the image signals output from the image sensor 48, and the light guide 41 that guides the illumination light supplied from the light source device 14 to an illumination window are inserted through the insertion part 12a illustrated in FIG. 1.

As illustrated in FIG. 2, the processor device 16 has an image acquisition unit 54, a correction amount calculation unit 60, an image processing unit 61, a display controller 66, and a controller 69. The processor device 16 is equivalent to a processor of the invention.

The image acquisition unit 54 obtains the image signals from the individual pixels of the image sensor 48 and acquires captured images in a plurality of colors, which are obtained by imaging the observation object using the image sensor 48. Specifically, the image acquisition unit 54 acquires a set of the B image, the G image, and the R image for each imaging frame. Additionally, the image acquisition unit 54 has the DSP 56, a noise reduction unit 58, and a converting unit 59, and performs various kinds of processing on the acquired captured images using these units. For example, the R signal, the G signal, and the B signal obtained as the sensor signals from the individual pixels of the image sensor 48 are output to the correction amount calculation unit 60 and the controller 69.

The DSP 56 performs various kinds of processing, such as defect correction processing, offset processing, gain correction processing, linear matrix processing, gamma conversion processing, demosaicing processing, and YC conversion processing, on the acquired captured images, as needed. Additionally, in the DSP 56, brightness values are obtained from the sensor signals of the image sensor 48 input as the image signals. In addition, for example, the G signal may be used as a brightness value.

The defect correction processing is the processing of correcting the pixel value of a pixel corresponding to a defective pixel of the image sensor 48.

The offset processing is the processing of reducing a dark current component from the images subjected to the defect correction processing and setting an accurate zero level.

The gain correction processing is the processing of adjusting a signal level of each image by multiplying the images subjected to the offset processing by a gain.

The linear matrix processing is the processing of enhancing color reproducibility on the images subjected to the offset processing, and the gamma conversion processing is the processing of adjusting the brightness or saturation of the image after the linear matrix processing.

The demosaicing processing (also referred to as equalization processing or synchronization processing) is the processing of interpolating the pixel value of a missing pixel and is performed on the images after the gamma conversion processing. The missing pixel is a pixel with no pixel value because pixels in other colors are disposed in the image sensor 48 due to the arrangement of color filters. For example, since the B image is an image obtained by imaging the observation object in the B pixel, there is no pixel value in pixels at positions corresponding to the G pixel and the R pixel of the image sensor 48. In the demosaicing processing, the pixel values of the pixels at the positions of the G pixel and the R pixel of the image sensor 48 are generated by interpolating the B image.

The YC conversion processing is the processing of converting the images after the demosaicing processing into a luminance channel Y, a color difference channel Cb, and a color difference channel Cr.

The noise reduction unit 58 performs noise reduction processing using, for example, a moving average method, a median filter method, or the like, on the luminance channel Y, the color difference channel Cb, and the color difference channel Cr.

The converting unit 59 re-converts the luminance channel Y, the color difference channel Cb, and the color difference channel Cr after the noise reduction processing into images in respective colors of BGR.

The correction amount calculation unit 60 performs correction for maintaining the hue of the endoscopic image, and performs white balance processing and the like to be described below.

The image processing unit 61 performs color conversion processing, color enhancement processing, and structure enhancement processing on the B image, the G image, and the R image, equivalent to one imaging frame, subjected to the above various kinds of processing to generate an observation image. In the color conversion processing, 3×3 matrix processing, grayscale conversion processing, three-dimensional look-up table (LUT) processing, or the like is performed on the images in the individual colors of BGR. The color enhancement processing is the processing of enhancing the colors of an image, and the structure enhancement processing is the processing of enhancing, for example, the tissue or structure of the observation object, such as blood vessels and pit patterns.

The display controller 66 sequentially acquires observation images from the image processing unit 61, converts the acquired observation images into a format suitable for display, and sequentially outputs and displays the converted images to and on the monitor 18. Accordingly, a doctor or the like can observe the observation object using still images or moving images of the observation images.

The controller 69 has, for example, a central processing unit (CPU), and performs overall control of the endoscope system 10, such as emission timing of the illumination light and synchronous control of an imaging frame. Additionally, in a case where the endoscope system 10 has the plurality of observation modes, the controller 69 switches the illumination light via the light source controller 22 by receiving an operation input from the mode changeover switch 13b. Accordingly, the observation mode is switched.

The processor device 16 is electrically connected to the monitor 18 and the operation input part 19. The monitor 18 outputs and displays the observation images, accompanying image information, and the like if necessary. The operation input part 19 functions as a user interface that receives an input operation, such as a function setting. In addition, an external recording unit (not illustrated) that records the images, the image information, and the like may be connected to the processor device 16.

Figure 5:
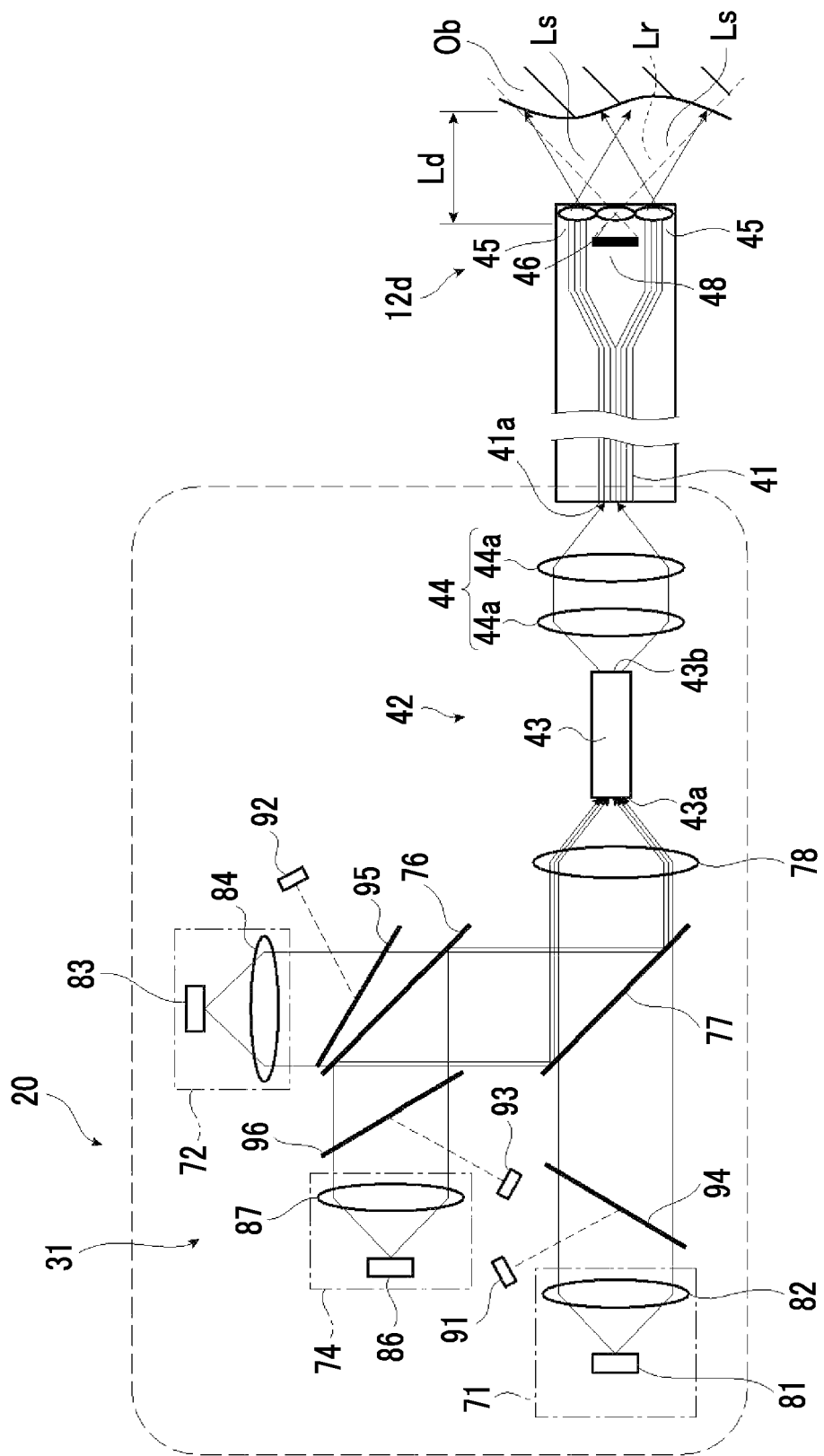
FIG. 5 is a schematic view illustrating an example of a light source unit of the endoscope system of the first embodiment of the invention.

Hereinafter, the configuration and the operation of the light source device 14 will be described in more detail. FIG. 5 is a schematic view illustrating an example of the light source unit of the endoscope system of the first embodiment of the invention.

As illustrated in FIG. 5, the light source unit 20 of the light source device 14 has a first light source 71, a second light source 72, a third light source 74, and a light path unit 42. The first light source 71, the second light source 72, and the third light source 74 can be respectively and independently controlled. Additionally, the light source unit 20 comprises a cooling member, such as a heat sink, that cools light emitting elements of individual light sources of the first light source 71, the second light source 72, and the third light source 74.

In the light source device 14, the light emitted from the light source unit 20 passes through the light guide 41, and is radiated to the object Ob as the illumination light Ls. Light from the light path unit 42 of the light source unit 20 is incident on the incident end 41a of the light guide 41. Reflected light Lr of the illumination light Ls radiated to the object Ob is incident on the image sensor 48 via the objective lens 46.

First light emitted by the first light source 71 is incident on the light guide 41 via a multiplexing member 77 that allows the first light to pass therethrough, a lens 78, and light path unit 42.

A beam splitter 94 is provided between the first light source 71 and the multiplexing member 77. A portion of the first light emitted by the first light source 71 is reflected in a predetermined ratio by the beam splitter 94. The light reflected by the beam splitter 94 is received by a photodetector 91. The light source controller 22 automatically and accurately controls the light emission quantity of the first light of the first light source 71 using the quantity of the light detected by the photodetector 91.

Second light emitted by the second light source 72 is incident on the light guide 41 via a multiplexing member 76 and the multiplexing member 77, which transmit the second light, the lens 78, and the light path unit 42.

A beam splitter 95 is provided between the second light source 72 and the multiplexing member 76. A portion of the second light emitted by the second light source 72 is reflected in a predetermined ratio by the beam splitter 95. The light reflected by the beam splitter 95 is received by a photodetector 92. The light source controller 22 automatically and accurately controls the light emission quantity of the second light of the second light source 72 using the quantity of the light detected by the photodetector 92.

Third light emitted by the third light source 74 is incident on the light guide 41 via a multiplexing member 76 and the multiplexing member 77, which allow the third light to be transmitted therethrough, the lens 78, and the light path unit 42.

A beam splitter 96 is provided between the third light source 74 and the multiplexing member 76. A portion of the third light emitted by the third light source 74 is reflected in a predetermined ratio by the beam splitter 96. The light reflected by the beam splitter 96 is received by a photodetector 93. The light source controller 22 automatically and accurately controls the light emission quantity of the light of the third light source 74 using the quantity of the light detected by the photodetector 93.

The photodetectors 91, 92, and 93 generate, for example, a light quantity measurement signal corresponding to the light quantity, and output the generated light quantity measurement signal to the light source controller 22. For example, as the light quantity increases, the value of the light quantity measurement signal increases. Further, the photodetectors 91, 92, and 93 receives a portion of the light from all light sources until the light paths are integrated by the light path integration part 31, and as long as information on the light quantity can be obtained, the arrangement position is not limited to that described above.

The light path integration part 31 integrates the respective light paths of color light emitted by the first light source 71, the second light source 72, and the third light source 74 into one light path to thereby multiplex light emitted from the first light source 71, the second light source 72, and the third light source 74. The light path integration part 31 is constituted by multiplexing members 76, 77 and a lens 78.

The light path integration part 31 multiplexes and integrates the light emitted from the first light source 71, the second light source 72, and the third light source 74, and emits the integrated light into to the incident end 41a of the light guide 41 of the endoscope 12 via the light path unit 42.

The light source unit 20 includes the light path unit 42 to which integrated light emitted from the light path integration part 31, that is, multiplexed light is incident.

The light path unit 42 includes the light guide part 43 and a light collecting part 44 that collects the light passing through the light guide part 43.

The light guide part 43 is an optical member having a homogenizing function, and can reflect light multiple times to obtain a uniform plane light source. In the light guide part 43, the light integrated by the light path integration part 31 is incident on the incident end 43a, and the integrated light is emitted from an exit end 43b. The light emitted from the exit end 43b of the light guide part 43 is incident on the light collecting part 44. Further, return light from the light guide 41 is incident on the exit end 43b in the light guide part 43. However, in this case, the light quantity of the return light is reduced by the homogenizing function of the light guide part 43 and the light with the reduced light quantity is emitted from the incident end 43a. The light guide part 43 is, for example, a light pipe.

The configuration of the light pipe as the light guide part 43 is not particularly limited, and for example, a polygonal shape is used. The outer periphery of the light pipe may be covered with a covering material. The covering material is made of, for example, a metal such as a steel-special-use stainless (SUS).

Besides the light pipe, an optical member having a core material (not illustrated) and a clad material (not illustrated) provided around the core material and having a smaller refractive index than the core material can be used for the light guide part 43.

The light collecting part 44 causes the light passing through the light guide part 43 to be incident on the light guide 41, and collects the light emitted from the exit end 43b of the light guide part 43 on the incident end 41a of the light guide 41. The configuration of the light collecting part 44 is not particularly limited, and, for example, two biconvex lenses 44a and 44b are arranged with their curved surfaces facing each other.

In addition, for the light collecting part 44, two plano-convex lenses (not illustrated) may be arranged such that flat surfaces thereof face each other in plane, or even two plano-convex lenses (not illustrated) may be arranged such that curved surfaces thereof face each other.

For the light collecting part 44, an imaging optical system can be used. In this case, the imaging magnification is not particularly limited, and, for example, the magnification is appropriately determined depending on the size of the incident end 41a of the light guide 41, and may be equal magnification. Further, in the case of the light collecting part 44 and the light guide 41, the incident end 41a of the light guide 41 may be disposed at the focal position of the biconvex lens 44b of the light collecting part 44, and the position of the incident end 41a may be provided out of the focal position of the biconvex lens 44b.

The multiplexed light is incident on the incident end 41a of the light guide 41 through the light path unit 42 by providing the light path unit 42. For example, in a case where the light reflected by the incident end 41a of the light guide 41 is incident on the light path unit 42 as return light, the return light is homogenized in the light guide part 43 by the homogenizing function of the light guide part 43, and the light quantity of the return light is smaller than that without the light path unit 42. As a result, the light quantity detected by the photodetectors 91, 92, and 93 is suppressed so as not to be greater than the actual light quantity, and the measurement accuracy of the light quantity as a reference of light quantity control by the photodetectors 91, 92, and 93 is increased, which makes it possible to perform the light quantity control appropriately at the time of controlling the light emission quantity of each light source. For this reason, for example, the accuracy in controlling the light quantity of the illumination light Ls can be increased such that the brightness value is constant.

The multiplexing member 76 and the multiplexing member 77 are, for example, dichroic mirrors, dichroic prisms, or the like. The lens 78 is an optical member for causing the integrated light to be incident on the incident end 43a of the light guide part 43.

It is preferable that the multiplexing member 76, the multiplexing member 77, the lens 78, the light guide part 43, and the biconvex lenses 44a and 44b each have an antireflection layer. In this way, return light and the like can be suppressed.

The photodetectors 91, 92, and 93 are, for example, photomultiplier tubes using a photoelectric effect, photoconductive elements, such as CdS or PbS, using electric resistance changes caused by photoirradiation, photoelectromotive force type photodiodes using a pn junction of or a semiconductor, or the like.

Further, each of the photodetectors 91, 92, and 93 may be provided with a wavelength limiting filter (not illustrated) for blocking light of a specific wavelength of incident light. The provision of the wavelength limiting filter makes it possible to improve the measurement accuracy of the light quantity of light with a wavelength to be measured.

The light to be emitted is not particularly limited as long as the first light source 71, the second light source 72, and the third light source 74 emit light having different wavelengths. Hereinafter, the first light source 71, the second light source 72, and the third light source 74 will be described in a specific example.

The first light source 71 comprises a light emitting element 81 that emits the first light including two color components with mutually different wavelengths, and a lens 82 that shapes the first light emitted by the light emitting element 81 into parallel light or the like. The light emitting element 81 is, for example, a semiconductor element, such as a light emitting diode (LED) or a laser diode (LD) having an emission spectrum including the first color component and the second color component out of the two color components with mutually different wavelengths.

The first light source 71 is, for example, a light source that emits light (hereinafter, referred to as green light) having a green component including two color components with mutually different wavelengths, in which the first color component is green and the second color component is red. Light of one color is used as light of two colors. The green light is also referred to as light showing green.

The second light source 72 comprises a light emitting element 83 that emits the second light as light of the color other than the above-described two color components with mutually different wavelengths, and a lens 84 that shapes the second light emitted by the light emitting element 83 into parallel light or the like. The light emitting element 83 is, for example, a semiconductor element, such as an LED or an LD.

Out of the two color components with mutually different wavelengths in the first light source 71, for example, in a case where the first color component is green and the second color component is red, the second light source 72 emits light (hereinafter referred to as blue light) including a blue component. The blue light is also referred to as light showing blue.

In the first light source 71, blue light in which the first color component is blue and the second color component is green may be used. In this case, a light source that emits light (hereinafter referred to as red light) including a red component is used as the second light source 72. The red light is also referred to as light showing red.

The two color components with mutually different wavelengths mean that the number of separable color components is two. Here, as described above, the blue light is light having a wavelength of about 440 nm or more and less than about 490 nm. The green light is light having a wavelength of about 490 nm or more and less than about 600 nm. The red light is light having a wavelength of about 600 nm or more and less than about 680 nm. For example, light having a wavelength range of 490 nm to 700 nm includes the above-described green light and red light. For example, light having a wavelength range of 440 nm to 600 nm includes the above-described blue light and green light.

In two or more light sources with different dominant wavelengths, the different dominant wavelengths mean that peak wavelengths of light emitted by individual light sources are not the same wavelength, and central wavelengths are not the same wavelength in a case where there is no peak wavelength. The same range of the peak wavelengths or the central wavelengths is appropriately determined in accordance with the specification or the like of the endoscope system 10.

The third light source 74 emits, for example, light (hereinafter referred to as violet light) including a violet component. The third light source 74 comprises a light emitting element 86, and a lens 87 that shapes the violet light emitted by the light emitting element 86 into parallel light or the like. The light emitting element 86 is, for example, a semiconductor element, such as an LED or an LD. The violet light emitted by the third light source 74 is incident on the light guide 41 via the multiplexing member 76 that reflects the violet light, the multiplexing member 77 that reflects the violet light, and the light path unit 42. The violet component of the violet light is received by the B pixel in the image sensor 48. For this reason, the reflected light of the violet light contributes to the B image together with the reflected light of the blue light, or the like.

In the normal observation mode, the light source controller 22 turns the first light source 71 and the second light source 72 and turns off the third light source 74. Meanwhile, in the blood vessel enhancement observation mode, the light source controller 22 turns on all the first light source 71, the second light source 72, and the third light source 74.

In a case where the first light source 71 emits the green light in which the first color component is green and the second color component is red and the second light source 72 emits the blue light, in the normal observation mode, light including the green light and the red light emitted by the first light source 71 and the blue light emitted by the second light source 72 are multiplexed to generate broadband white light. Meanwhile, in the blood vessel enhancement observation mode, mixed light in which violet light having a high absorbance for hemoglobin in blood is mixed with the white light is generated. In addition, in the blood vessel enhancement observation mode, the light source controller 22 lowers the ratio of the quantity of the blue light such that the violet light becomes more dominant than the blue light.

Figure 6:
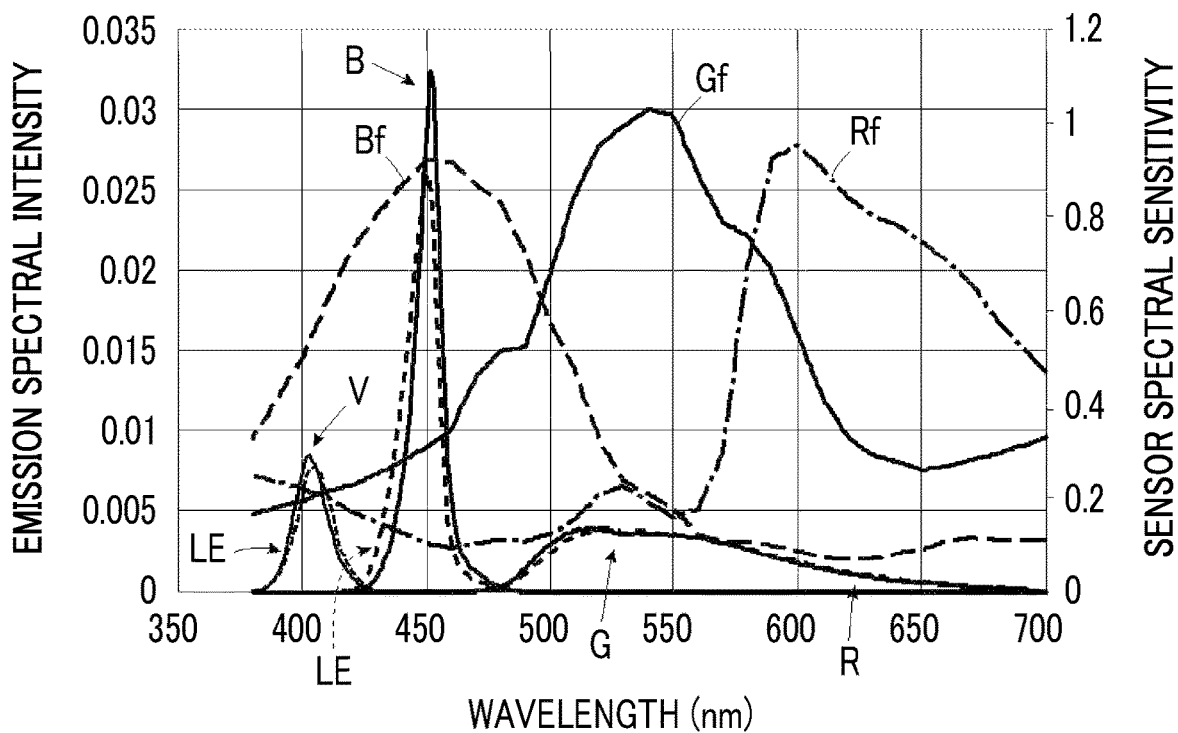
FIG. 6 is a graph illustrating an example of an emission spectrum of the light source unit and spectral sensitivity of the image sensor in the endoscope system of the first embodiment of the invention.

In the light source device 14 of the above-described configuration, the light emitted from the light source unit 20 of the light source device 14, that is, the illumination light Ls (refer to FIG. 5), which passes through the light guide 41 of the endoscope 12 and is emitted from the distal end part 12d of the endoscope, has, for example, an emission spectrum LE illustrated in FIG. 6.

FIG. 6 is a graph illustrating an example of the emission spectrum of the light source unit and the spectral sensitivity of the image sensor in the endoscope system of the first embodiment of the invention.

In addition, in the emission spectrum LE illustrated in FIG. 6, symbol V represents the violet light, symbol B represents the blue light, symbol G represents the green light, and symbol R represents the red light. Additionally, in the emission spectrum LE illustrated in FIG. 6, a solid line shows that the light quantity is relatively low, and a dashed line shows that the light quantity is relatively high.

In the emission spectrum LE illustrated in FIG. 6, a peak wavelength is present near the wavelength of 400 nm and a peak wavelength is present near the wavelength of 450 nm. The peak wavelength near the wavelength of 400 nm is based on the violet light emitted by the third light source 74, and the peak wavelength near the wavelength of 450 nm is based on the blue light emitted by the second light source 72.

Light having a wavelength of 470 nm to 700 nm is based on the green light emitted by the first light source 71, and includes green and red as color components.

The emission spectrum LE illustrated in FIG. 6 represents substantially white light. In the endoscope system 10, the observation object is imaged with the reflected light Lr of the illumination light Ls having the emission spectrum LE including the blue light, the green light, and the red light by using the image sensor 48 having a spectral sensitivity characteristic illustrated in FIG. 6. Symbol Bf illustrated in FIG. 6 represents a spectral sensitivity for the light showing blue. Symbol Gf represents a spectral sensitivity for the light showing green. Symbol Rf represents a spectral sensitivity for the light showing red. The spectral sensitivity Bf and the spectral sensitivity Gf have an overlapping wavelength range, and the spectral sensitivity Gf and the spectral sensitivity Rf have an overlapping wavelength range. The spectral sensitivity is not limited to these.

The image sensor 48 has the first element part 48a, the second element part 48b, and the third element part 48c as described above. For example, the first element part 48a has the spectral sensitivity Gf for the light showing green. The second element part 48b has the spectral sensitivity Rf for the light showing red. The third element part 48c has the spectral sensitivity Bf for the light showing blue.

Additionally, the first light source 71 may be configured to have a light emitting diode having a light emission peak between the peak wavelength of the spectral sensitivity of the first element part 48a and the peak wavelength of the spectral sensitivity of the second element part 48b. In this case, in a case where the first element part 48a has the spectral sensitivity Gf and the second element part 48b has the spectral sensitivity Rf, a light emitting diode having a light emission peak in a wavelength of 550 to 600 nm is used. In a case where the first element part 48a has the spectral sensitivity Bf and the second element part 48b has the spectral sensitivity Gf, a light emitting diode having a light emission peak in a wavelength of 450 to 550 nm is used.

In addition to the above configuration, as the light source, the first light source 71 may be a light source that emits red light, the second light source 72 may be a light source that emits green light, and the third light source 74 may be a light source that emits blue light.

The image sensor 48 images the observation object using the light emitted from first light source 71 of the light source unit 20, and the first signal value of the first color component obtained by the first element part 48a of the image sensor 48 and the second signal value of the second color component obtained by the second element part 48b are obtained in the processor device 16. The processor device 16 calculates a signal ratio between the first signal value and the second signal value, and sets the signal ratio to a predetermined set value by changing at least one signal value out of the first signal value and the second signal value.

In the image sensor 48, the first signal value of the first color component is obtained in the first element part 48a, the second signal value of the second color component is obtained in the second element part 48b, and a third signal value of light of a color other than the two color components is obtained in the third element part 48c.

Then, the first signal value and the second signal value are output from the DSP 56 to the correction amount calculation unit 60. In the correction amount calculation unit 60, the signal ratio is obtained between the first signal value and the second signal value, and the signal ratio is set to the predetermined set value by changing at least one signal value out of the first signal value and the second signal value.

Additionally, the signal ratio may be set to the predetermined set value by changing at least one signal value among the first signal value, the second signal value, and the third signal value in accordance with the light quantity. In this case, the first signal value, the second signal value, or the third signal value, which changes in accordance with the light quantity, is determined, the changing value is obtained as a correction coefficient, and the correction coefficient is stored in the correction amount calculation unit 60.

For example, a brightness value is calculated using at least one among the first signal value, the second signal value, or the third signal value, and the light quantity of the first light source 71 is specified on the basis of the brightness value. Also, the signal ratio may be set to the predetermined set value by changing at least one signal value among the first signal value, the second signal value, and the third signal value in accordance with the light quantity with one signal value among the first signal value, the second signal value, and the third signal value as a reference value. Being set to such a set value is also referred to as white balance processing. Through the white balance processing, the tint of the endoscopic image can be made constant irrespective of the light quantity.

In this case, in the correction amount calculation unit 60, the first signal value, the second signal value, or the third signal value that is used as the reference value is determined, the first signal value, the second signal value, or the third signal value that changes in accordance with the light quantity is determined, the changing value is obtained as a correction coefficient, and the correction coefficient is stored in the correction amount calculation unit 60.

In addition, in the above description, one signal value is used as the reference value, but the invention is not limited thereto. Additionally, the signal ratio may be set to the predetermined set value by changing at least one signal value among the first signal value, the second signal value, and the third signal value in accordance with the light quantity without setting the reference value.

Figure 7:
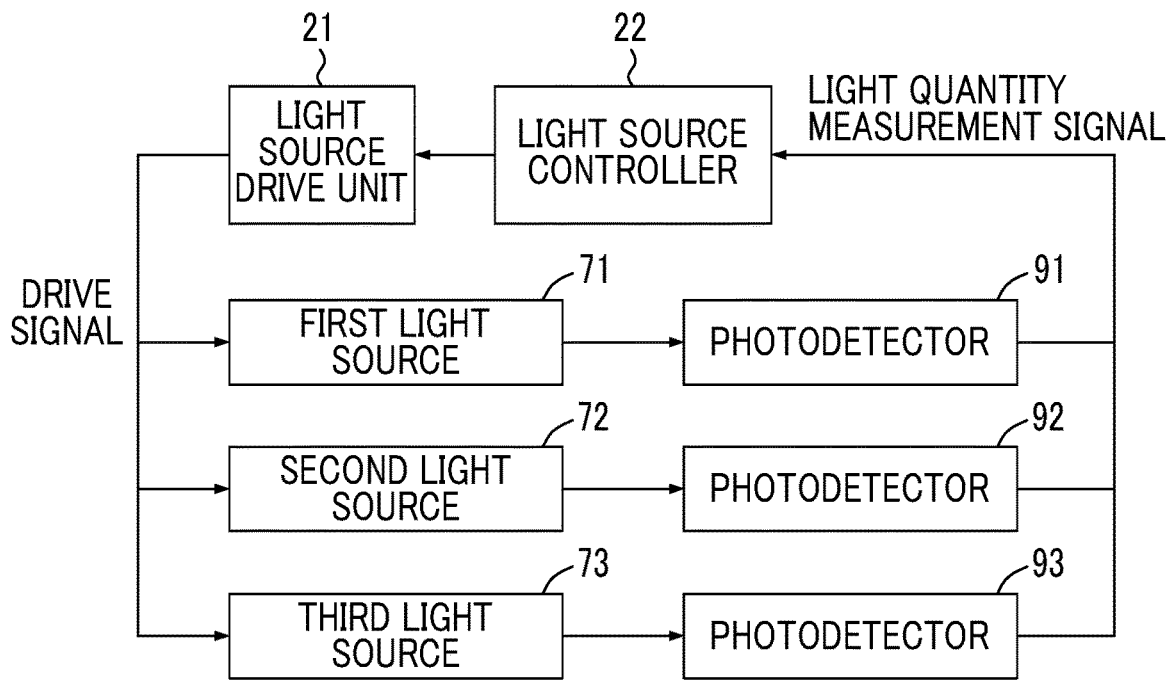
FIG. 7 is a schematic view illustrating an example of a configuration for performing light quantity control.

FIG. 7 is a schematic view illustrating an example of a configuration for performing light quantity control.

Each of the photodetectors 91, 92, and 93 receives light that is reflected by the beam splitters 94, 95, and 96, outputs the light quantity measurement signal according to each light quantity of received light as illustrated in FIG. 7, and outputs the light quantity measurement signal to the light source controller 22. The light source controller 22 compares the light quantity measurement signal with the target light quantity, and based on the comparison result, the drive signals supplied to the first light source 71, the second light source 72, and the third light source 73 are adjusted in the light source drive unit 21 such that the light quantity becomes the target value.

Thus, each of the light quantities of the first light source 71, the second light source 72, and the third light source 73 are constantly monitored by the photodetectors 91, 92, and 93 and by adjusting the drive signal to be supplied based on the measurement result of the light quantity, the light quantity can be controlled so as to be kept at the target value. The measurement accuracy of the light quantity is high because the return light is suppressed. Therefore, it is possible to stably obtain illumination light of a target emission spectrum with higher accuracy.

In addition, the configuration of the light source unit 20 is not limited to the configuration illustrated in the above-described FIG. 5.

Figure 8:
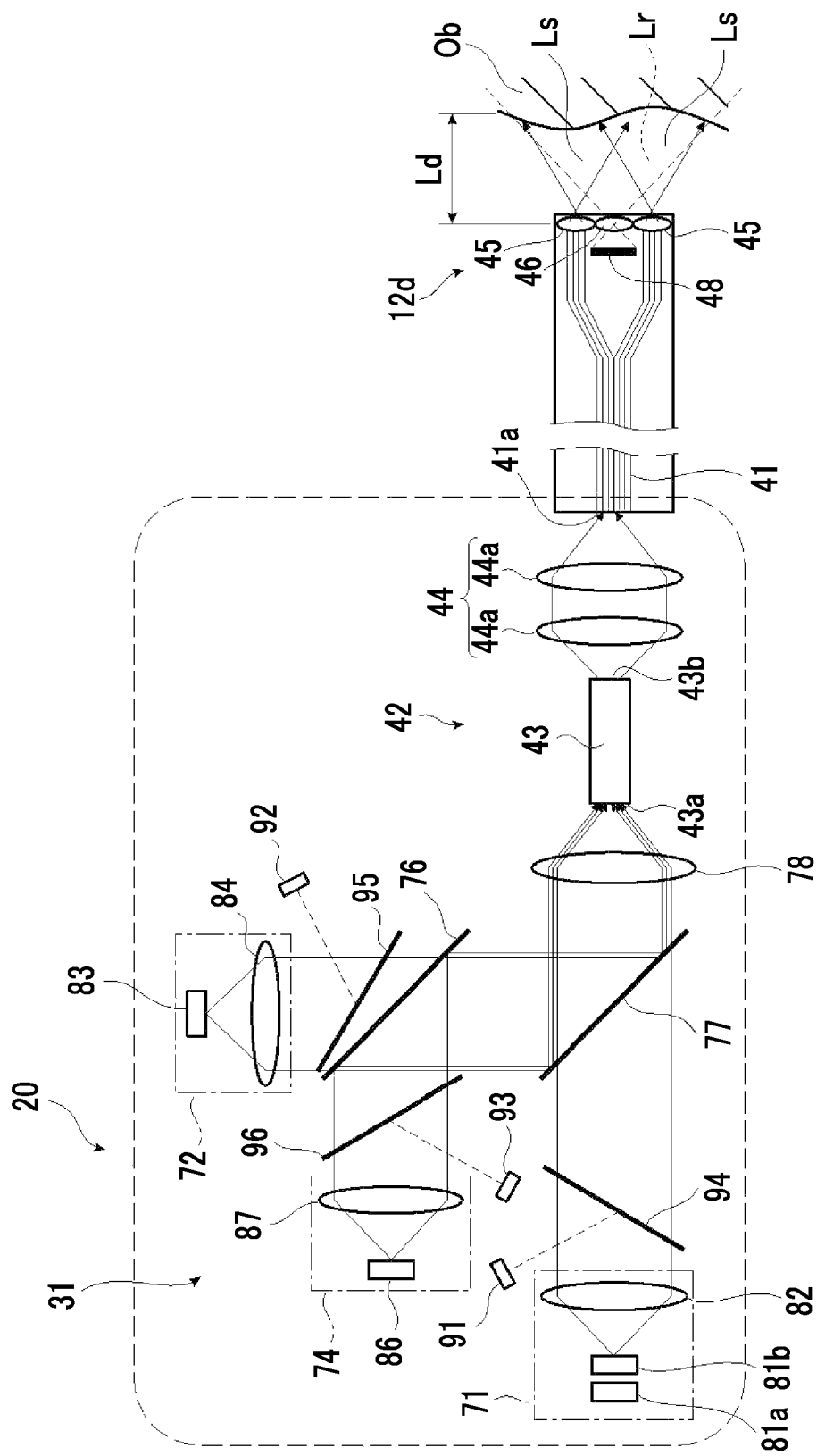
FIG. 8 is a schematic view illustrating a modification example of the example of the light source unit of the endoscope system of the first embodiment of the invention.

FIG. 8 is a schematic view illustrating a modification example of the example of the light source unit of the endoscope system of the first embodiment of the invention.

Since the light source unit 20 illustrated in FIG. 8 is different from the light source unit 20 illustrated in FIG. 5 in the configuration of the first light source 71 and the other configuration thereof is the same as that of the light source unit 20 illustrated in FIG. 5, the detailed description thereof will be omitted.

The first light source 71 illustrated in FIG. 8 has a light emitting element 81a that emits excitation light, and a fluorescent body 81b that emits light including two color components with mutually different wavelengths as the excitation light emitted by the light emitting element 81a is incident thereon.

In the first light source 71, for example, the excitation light emitted by the light emitting element 81a is blue light having a peak in about 445 nm, and the light emitted by the fluorescent body 81b is broadband green light includes the red component in addition to the green component. In addition to this, the first light source 71 may emit broadband blue light including the green component in addition to the blue component by changing the wavelength of the excitation light emitted by the light emitting element 81a, and the fluorescent body 81b.

Second Embodiment

Next, a second embodiment will be described.

Figure 9:
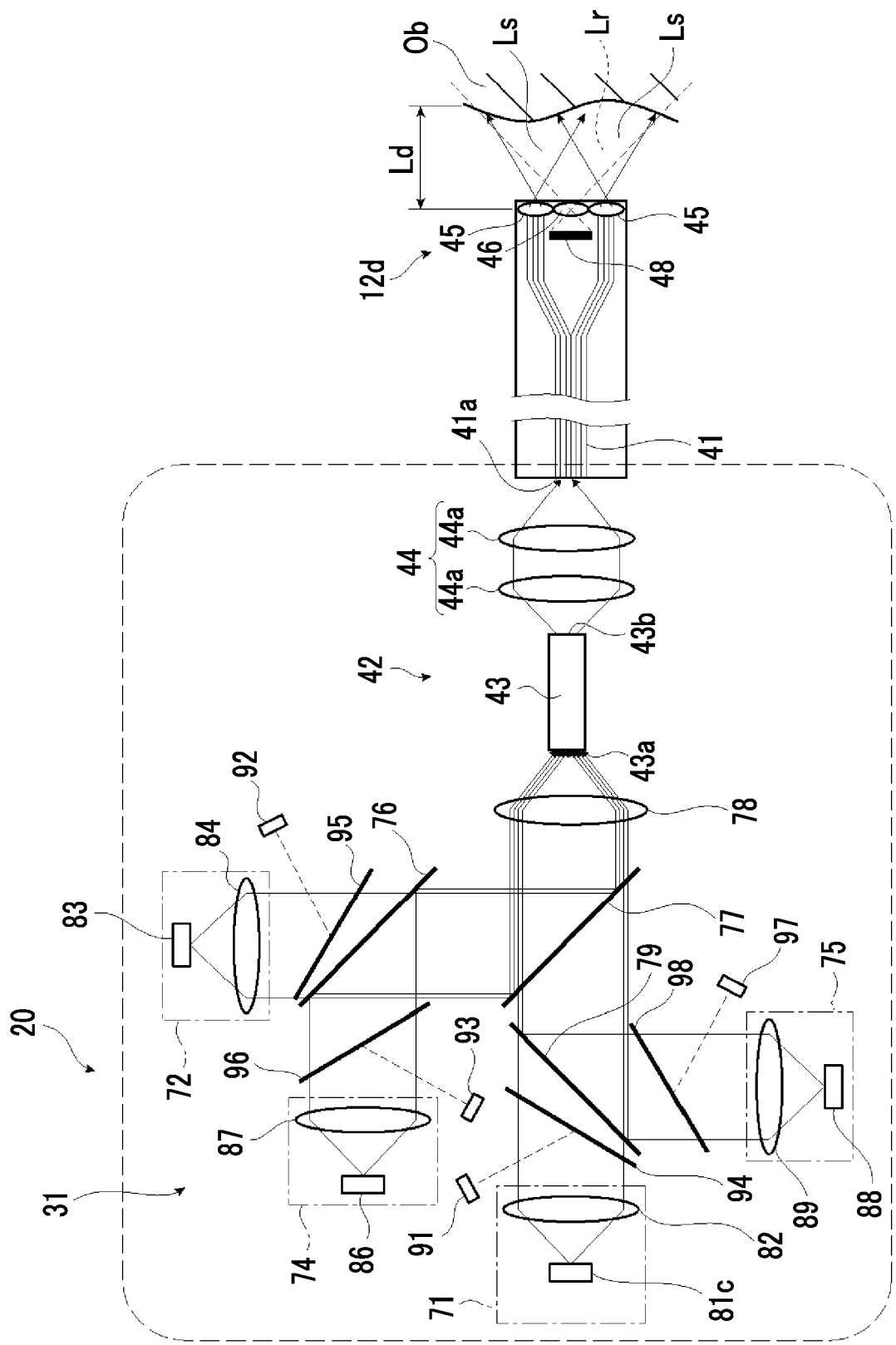
FIG. 9 is a schematic view illustrating an example of a light source unit of an endoscope system of a second embodiment of the invention.

FIG. 9 is a schematic view illustrating an example of the light source unit of the endoscope system of the second embodiment of the invention.

The second embodiment is different in the configuration of the light source unit. Since the configuration of the light source unit 20 illustrated in FIG. 9 is different from the light source unit 20 illustrated in FIG. 5 in that the number of light sources is four, and the other configuration thereof is the same as that of the light source unit 20 illustrated in FIG. 5, the detailed description thereof will be omitted.

The light source unit 20 illustrated in FIG. 9 has a fourth light source 75. In the light source unit 20 illustrated in FIG. 5, the light including the two color components with mutually different wavelengths is emitted from the first light source 71. However, in the light source unit 20 illustrated in FIG. 9, light of the first color component is emitted from the first light source 71, and light of the fourth color component is emitted as fourth light from the fourth light source 75.

A multiplexing member 79 is provided between the first light source 71 and the multiplexing member 77. The multiplexing member 79 transmits the light emitted by the first light source 71. The multiplexing member 79 multiplexes the light of the first color component emitted by the first light source 71 and the light of the fourth color component emitted by the fourth light source 75, and guides the multiplexed light to the multiplexing member 77.

The fourth light source 75 comprises a light emitting element 88 that emits the light of the fourth color component as the fourth light, and a lens 89 that shapes the light emitted by the light emitting element 88 into parallel light or the like. The light emitting element 88 is, for example, a semiconductor element, such as an LED or an LD. The fourth light emitted by the fourth light source 75 is reflected by the multiplexing member 79, passes through the light path unit 42 via the multiplexing member 77 and is incident on the light guide 41.

A beam splitter 98 is provided between the fourth light source 75 and the multiplexing member 79. A portion of the fourth light emitted by the fourth light source 75 is reflected in a predetermined ratio by the beam splitter 98. The light reflected by the beam splitter 98 is received by a photodetector 97. The light source controller 22 automatically and accurately controls the light emission quantity of the fourth light of the fourth light source 75 using the quantity of the light detected by the photodetector 97.

The multiplexing member 79 has the same configuration as the multiplexing member 76 and the multiplexing member 77, and is, for example, a dichroic mirror, a dichroic prism, or the like.

The photodetector 97 has the same configuration as the above-described photodetectors 91, 92, and 93. Further, the arrangement position of the photodetector 97 is the position where a portion of the light is received until the light paths are integrated by the light path integration part 31, similarly to the above-described photodetectors 91, 92, and 93, and as long as information on the light quantity can be obtained, the arrangement position is not limited to that described above.

The first light source 71, the second light source 72, the third light source 74, and the fourth light source 75 can be respectively and independently controlled. The first light source 71, the second light source 72, the third light source 74, and the fourth light source 75 are constructed to have the same configuration as the three components in the light source units 20 illustrated in FIGS. 5 and 8, and have a semiconductor element such as LED or LD.

A light emitting element 81c of the first light source 71 emits the green light, for example, as the light of the first color component. The light emitting element 88 of the fourth light source 75 emits, for example, the red light as the light of the fourth color component.

Additionally, the light emitting element 81c of the first light source 71 may emit, for example, the blue light as the light of the first color component, the light emitting element 88 of the fourth light source 75 may emit, for example, the green light as the light of the second color component, and the second light source 72 may emit the red light.

For example, green light is emitted by the first light source 71, blue light is emitted by the second light source 72, violet light is emitted by the third light source 73, and red light is emitted by the fourth light source 75.

For example, the spectral sensitivity of the image sensor 48 illustrated in FIG. 9 is the same as the spectral sensitivity of the image sensor 48 illustrated in FIG. 5.

Figure 10:
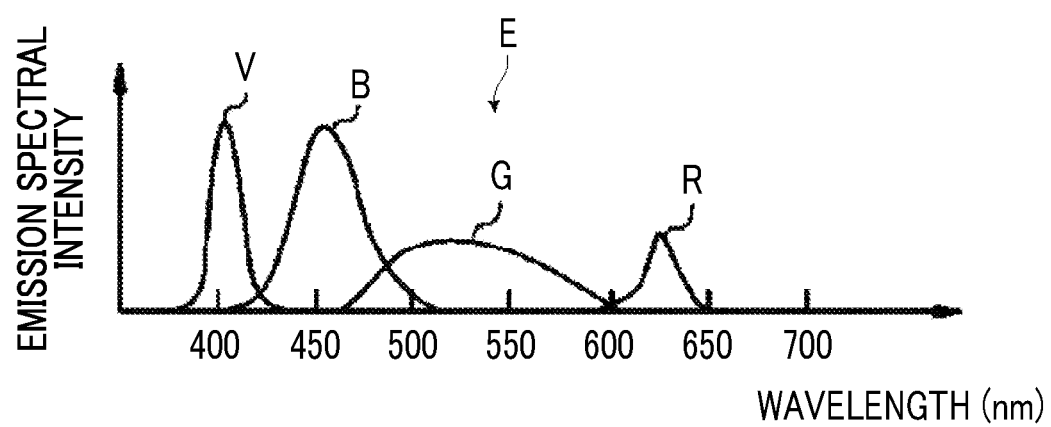
FIG. 10 is a graph illustrating an example of an emission spectrum of the light source unit of the endoscope system of the second embodiment of the invention.

FIG. 10 is a graph illustrating an example of an emission spectrum of the light source unit of the endoscope system of the second embodiment of the invention.

By the first light source 71, the second light source 72, the third light source 74, and the fourth light source 75, for example, an emission spectrum E illustrated in FIG. 10 is obtained. The emission spectrum LE illustrated in FIG. 10 includes red light R, green light G, blue light B, and violet light V.

For example, the red light R has a wavelength range of 615 nm to 635 nm and a central wavelength of 620±10 nm. The green light G has, for example, a wavelength range of 500 nm to 600 nm and a central wavelength of 520±10 nm.

The blue light B has, for example, a wavelength range of 440 nm to 470 nm, and a central wavelength of 455±10 nm. The violet light V has, for example, a wavelength range of 395 nm to 415 nm and a central wavelength of 405±10 nm.

Also in the light source unit 20 illustrated in FIG. 9, the multiplexed light is incident on the incident end 41a of the light guide 41 through the light path unit 42 by providing the light path unit 42. For example, in a case where the light reflected by the incident end 41a of the light guide 41 is incident on the light path unit 42 as return light, the return light is homogenized in the light guide part 43 by the homogenizing function of the light guide part 43, and the light quantity of the return light is smaller than that without the light path unit 42. As a result, the light quantity detected by the photodetectors 91, 92, 93, and 97 is suppressed so as not to be greater than the actual light quantity, and the measurement accuracy of the light quantity as a reference of light quantity control by the photodetectors 91, 92, 93, and 97 is increased, which makes it possible to perform the light quantity control appropriately at the time of controlling the light emission quantity of each light source. For this reason, for example, the accuracy in controlling the light quantity of the illumination light Ls can be increased such that the brightness value is constant.

The light source unit 20 illustrated in FIG. 9 is configured to include four light sources, and at the time of performing the light quantity control, implement the same configuration as the configuration illustrated in FIG. 7 described above can be implemented.

Each of the photodetectors 91, 92, 93, and 97 receives light that is reflected by the beam splitters 94, 95, 96, and 98, generates the light quantity measurement signal according to each light quantity of received light, and outputs the light quantity measurement signal to the light source controller 22. The light source controller 22 compares the light quantity measurement signal with the target light quantity, and based on the comparison result, the drive signals supplied to the first light source 71, the second light source 72, the third light source 73, and the fourth light source 75 are adjusted in the light source drive unit 21 such that the light quantity becomes the target value.

Thus, each of the light quantities of the first light source 71, the second light source 72, the third light source 73, and the fourth light source 75 are constantly monitored by the photodetectors 91, 92, 93, and 97, and by adjusting the drive signal to be supplied based on the measurement result of the light quantity, the light quantity can be controlled so as to be kept at the target value. The measurement accuracy of the light quantity is high because the return light is suppressed. Therefore, it is possible to stably obtain illumination light of a target emission spectrum with higher accuracy.

Although a configuration has been described in which the light quantities are monitored by arranging photodetectors for all light sources in any of the light source unit 20 illustrated in FIG. 5 and FIG. 8 and the light source unit 20 illustrated in FIG. 9, the invention is not limited thereto. For example, a configuration may be achieved in which the light quantity is controlled by providing a photodetector only for the light source having a large light quantity fluctuation among a plurality of light sources. Among the plurality of light sources, at least one light source may be provided with the photodetector to control the light quantity.

The invention is basically configured as described above. Although the endoscope system of the invention has been described above in detail, it is natural that the invention is not limited to the above-described embodiment, and various improvements and modifications may be made without departing from the scope of the invention.

EXPLANATION OF REFERENCES

10: endoscope system
12: endoscope
12a: insertion part
12b: operating part
12c: bending part
12d: distal end part
12e: angle knob
13a: zooming operating part
13b: mode changeover switch
14: light source device for an endoscope, light source device
16: processor device
17: universal cord
18: monitor
19: operation input part
20: light source unit
21: light source drive unit
22: light source controller
30a: illumination optical system
30b: imaging optical system
31: light path integration part
41: light guide
41a: incident end
42: light path unit
43: light guide part
43a: incident end
43b: exit end
44: light collecting part
44a, 44b: biconvex lens
45: illumination lens
46: objective lens
47: zoom lens
48: image sensor
48a: first element part
48b: second element part
48c: third element part
49: pixel unit
49a: first pixel
49b: second pixel
49c: third pixel
50: filter unit
50B: B color filter
50G: G color filter
50R: R color filter
50a: first filter
50b: second filter
50c: third filter
54: image acquisition unit
58: noise reduction unit
59: converting unit
60: correction amount calculation unit
61: image processing unit
66: display controller
69: controller
71: first light source
72: second light source
73: third light source
74: third light source
75: fourth light source
76, 77, 79: multiplexing member
78, 82, 84, 87, 89: lens
81, 81a, 81c: light emitting element 81b: fluorescent body
83, 86, 88: light emitting element
91 92, 93, 97: photodetector
94 95, 96, 98: beam splitter
Bf: spectral sensitivity
Gf: spectral sensitivity
B: blue light
LE: emission spectrum
G: green light
R: red light
V: violet light
Ld: distance
Lr: reflected light
Ls: illumination light
Ob: object
Rf: spectral sensitivity

What is claimed is:

1. A light source device for an endoscope, the light source device comprising:
   a plurality of light sources that emits light with different wavelengths;
   a light path integration part that integrates light paths of light emitted from the plurality of light sources to emit integrated light;
   a light path unit on which the integrated light emitted from the light path integration part is incident;
   a photodetector that receives a portion of light emitted from at least one of the plurality of light sources until the light paths are integrated by the light path integration part to obtain information on a light quantity; and
   a light source controller that adjusts the light quantity of the light emitted from the at least one light source based on a light quantity measurement signal generated by the photodetector,
   wherein the light path unit includes
      a light guide part that has a homogenizing function to receive the integrated light from the light path integration part, and
      a light collecting part that collects light emitted from an exit end of the light guide part.

2. The light source device for an endoscope according to claim 1,
   wherein the light guide part is a light pipe.

3. The light source device for an endoscope according to claim 1,
   wherein the light guide part has a core material and a clad material provided around the core material and having a smaller refractive index than the core material.

4. The light source device for an endoscope according to claim 1,
   wherein the light collecting part is formed by arranging two biconvex lenses such that curved surfaces thereof face each other, arranging two plano-convex lenses such that flat surfaces thereof face each other, or arranging two plano-convex lenses such that curved surfaces thereof face each other.

5. The light source device for an endoscope according to claim 2,
   wherein the light collecting part is formed by arranging two biconvex lenses such that curved surfaces thereof face each other, arranging two plano-convex lenses such that flat surfaces thereof face each other, or arranging two plano-convex lenses such that curved surfaces thereof face each other.

6. The light source device for an endoscope according to claim 3,
   wherein the light collecting part is formed by arranging two biconvex lenses such that curved surfaces thereof face each other, arranging two plano-convex lenses such that flat surfaces thereof face each other, or arranging two plano-convex lenses such that curved surfaces thereof face each other.

7. The light source device for an endoscope according to claim 1,
   wherein the photodetector is provided to each of the plurality of light sources, and
   the light source controller adjusts the light quantity of the light emitted from each of the plurality of light sources based on the light measurement quantity signal generated by each of the photodetectors.

8. The light source device for an endoscope according to claim 2,
   wherein the photodetector is provided to each of the plurality of light sources, and
   the light source controller adjusts the light quantity of the light emitted from each of the plurality of light sources based on the light measurement quantity signal generated by each of the photodetectors.

9. The light source device for an endoscope according to claim 3,
   wherein the photodetector is provided to each of the plurality of light sources, and
   the light source controller adjusts the light quantity of the light emitted from each of the plurality of light sources based on the light measurement quantity signal generated by each of the photo detectors.

10. The light source device for an endoscope according to claim 4,
    wherein the photodetector is provided to each of the plurality of light sources, and
    the light source controller adjusts the light quantity of the light emitted from each of the plurality of light sources based on the light measurement quantity signal generated by each of the photodetectors.

11. The light source device for an endoscope according to claim 1,
    wherein the plurality of light sources is three or four in number.

12. The light source device for an endoscope according to claim 2,
    wherein the plurality of light sources is three or four in number.

13. The light source device for an endoscope according to claim 3,
    wherein the plurality of light sources is three or four in number.

14. The light source device for an endoscope according to claim 4,
    wherein the plurality of light sources is three or four in number.

15. The light source device for an endoscope according to claim 1,
    wherein the plurality of light sources includes a light source that emits red light, a light source that emits green light, and a light source that emits blue light.

16. The light source device for an endoscope according to claim 1,
    wherein the plurality of light sources includes a laser diode or a light emitting diode.

17. The light source device for an endoscope according to claim 1,
    wherein the photodetector is a photodiode.

18. An endoscope system comprising:
an endoscope that includes a light guide; and
a light source device for an endoscope that supplies light to the light guide,
wherein the light source device for an endoscope includes
- a plurality of light sources that emits light with different wavelengths,
- a light path integration part that integrates light paths of light emitted from the plurality of light sources to emit integrated light,
- a light path unit on which the integrated light emitted from the light path integration part is incident,
- a photodetector that receives a portion of light emitted from at least one of the plurality of light sources until the light paths are integrated by the light path integration part to obtain information on a light quantity, and
- a light source controller that adjusts the light quantity of the light emitted from the at least one light source based on a light quantity measurement signal generated by the photodetector, the light path unit includes
- a light guide part that has a homogenizing function to receive the integrated light from the light path integration part, and
- a light collecting part that collects light emitted from an exit end of the light guide part, and the integrated light, after passing through the light guide part of the light path unit, is supplied to the light guide through the light collecting part of the light path unit.

19. The endoscope system according to claim 18,
wherein the photodetector is provided to each of the plurality of light sources, and
the light source controller adjusts the light quantity of the light emitted from each of the plurality of light sources based on the light quantity measurement signal generated by each of the photodetectors.

* * * * *